United States Patent [19]

Rossi

[11] Patent Number: 5,145,351
[45] Date of Patent: Sep. 8, 1992

[54] APPARATUS FOR THE SHAPING OF ARTICLES OF HYGIENE

[75] Inventor: Guido Rossi, Zurich, Switzerland
[73] Assignee: Progesan SRL, Italy
[21] Appl. No.: 651,341
[22] PCT Filed: Apr. 26, 1990
[86] PCT No.: PCT/EP90/00673
  § 371 Date: Feb. 8, 1991
  § 102(e) Date: Feb. 8, 1991
[87] PCT Pub. No.: WO90/13278
  PCT Pub. Date: Nov. 15, 1990

[30] Foreign Application Priority Data

May 5, 1989 [CH] Switzerland ............... 1706/89
Jul. 24, 1989 [CH] Switzerland ............... 2757/89

[51] Int. Cl.$^5$ ............... B29C 43/02; B29C 43/06
[52] U.S. Cl. ............... 425/80.1; 425/81.1; 425/182; 425/388; 425/504; 425/506
[58] Field of Search ............... 425/81.1, 82.1, 388, 425/506, 508, 510, 511, 405.13, 80.1, 83.1, 505, 504, 182, 150.6; 264/517, 518, 119, 121

[56] References Cited

U.S. PATENT DOCUMENTS

| 2,086,757 | 7/1937 | Williams | 425/81.1 |
| 3,226,764 | 1/1966 | Hostettler | 425/80.1 |
| 3,844,288 | 10/1974 | Kiela | 128/287 |
| 3,846,871 | 11/1974 | Kolbach | 19/148 |
| 3,882,216 | 5/1975 | Delanty et al. | 264/121 |
| 3,939,240 | 2/1976 | Savich | 264/121 |
| 4,005,957 | 2/1977 | Savich | 425/80.1 |
| 4,598,441 | 7/1986 | Stemmler | 425/81.1 |
| 4,666,647 | 5/1987 | Enloe et al. | 425/80.1 |
| 4,761,258 | 8/1988 | Enloe | 425/80.1 |
| 4,859,388 | 8/1989 | Peterson et al. | 264/517 |
| 4,904,440 | 2/1990 | Angstadt | 264/518 |
| 4,915,897 | 4/1990 | Farrington et al. | 264/517 |

FOREIGN PATENT DOCUMENTS 3413925 10/1985 Fed. Rep. of Germany.
3710055 10/1988 Fed. Rep. of Germany.

*Primary Examiner*—Willard Hoag
*Attorney, Agent, or Firm*—Bachman & LaPointe

[57] ABSTRACT

In an apparatus for the shaping and compacting of absorbent pads for absorbing body fluid, which are intended for articles of hygiene and which consist of a plurality of part layers and, if appropriate, are treated with a superabsorbent agent, to form at least one absorbent-pad layer. A rotary band has arranged on it over the entire length of the rotary band, at distances from one another, trough-shaped insertion molds into which shaping insets can be inserted. Along the rotary band production devices are arranged, in twos respectively along the linear outward path and return path, and in the opposite direction to the rotary band there is a driving band which can be pressed against this, and furthermore there is arranged a thermal compacting device which has calender and/or embossing rollers following in the conveying direction and which consists of a heating cylinder with a pressure band arranged on it.

22 Claims, 3 Drawing Sheets

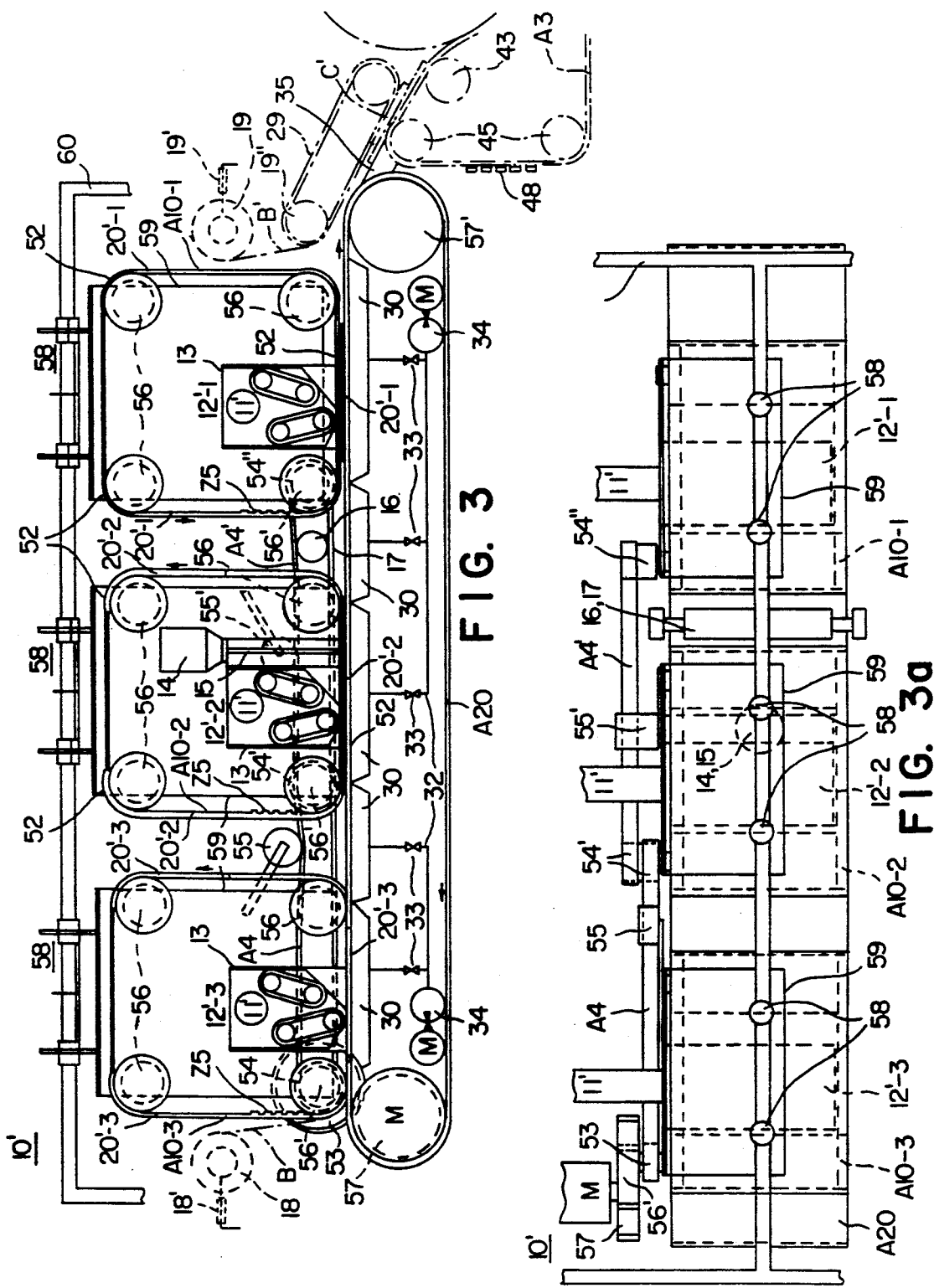

APPARATUS FOR THE SHAPING OF ARTICLES OF HYGIENE

BACKGROUND OF THE INVENTION

The invention relates to an apparatus for the shaping and compacting of absorbent pads for absorbing body fluid which consist of a plurality of part layers and which is intended for articles of hygiene, especially for the production of body-shaped absorbent pads for disposable baby napkins and disposable adult napkins, sanitary towels, insert slips and the like.

There are known apparatuses for the production of articles of hygiene, in which a web of material resembling an absorbent pad is guided continuously through a severing device, and the lateral edge regions of the web of material are thereby severed to the desired shape, for example for shaping the leg portions into a bobbin-like form for disposable napkins. Severing is carried out by punching out or sawing or by means of water-jet or air-jet cutting in an additional device, and at the same time hard edges can be obtained at the cutting points as a result of the compacting of the flocks. In continuous production, a severing device of this type can give rise to faults, and material waste is unavoidable, thus entailing an undesirable outlay and increasing the operating costs.

So that the absorbent pads do not have to be machined by shaping cutting during production, for example German Offenlegungsschrift 3,710,055 provides an apparatus for the continuous production of sanitary towels, in which a plurality of flock-depositing stations arranged over the circumference of a rotatable suction drum and having an air-permeable bottom are used. Each depositing point is equipped with a tool set which is mounted firmly on the suction drum and which comprises at least one shaping-shoe/flock-template unit, a press ram and a welding and, if appropriate, severing tool.

With such an arrangement of the individual processing devices, because of the complicated tool sets connected to lifting motors via lifting rods a conversion of the apparatus to other articles of hygiene demands a large amount of time and is possible only to a restricted extent, with the result that apparatuses of this type are only ever used as single-purpose machines.

A further disadvantage is that the feeding of superabsorbent agents from the periphery of the suction drum into the absorbent pads cannot be achieved to the best possible degree. The superabsorbent agent is introduced into a particular shaping recess and then transferred from this onto the flock web. This solution does not always ensure an exact filling of the shaping recesses, and therefore the quantity of this agent can fluctuate in the articles produced.

Another embodiment of an apparatus for the production of absorbent pads for absorbing body fluid is known from DE 3,413,925 A1. The apparatus consists of two so-called flock applicators of identical design, each of the two flock applicators being designed as a suction cylinder which has shaping recesses and which forms the so-called flock wheel. A first part layer of the absorbent pad to be produced is sucked onto the first flock wheel, and a second part layer is sucked onto the second flock wheel. By means of a transfer roller, the part layers produced on the first flock wheel are applied to the part layers produced on the second flock wheel. A further transfer roller lifts off the finished absorbent pads from the second flock wheel and transfers them to a further-processing machine by means of a suction belt. A possible addition of a superabsorbent agent can be provided between the two part layers forming the absorbent pads.

The apparatus is a single-purpose machine which is suitable only for a few articles of hygiene of similar design, but a more comprehensive conversion of the apparatus for different articles is hardly expedient. Another disadvantage is that only absorbent pads consisting of two part layers can be produced, because it is scarcely possible to connect further flock wheels and transfer rollers, especially where part layers of differing size are concerned.

A thermal compacting device which can be built into a continuous production line and is intended for an absorbent-pad web treated with superabsorbent agent and which makes use of a hot-air throughflow principle is likewise known. The air throughflow warms through on both sides, on two perforated drums, the absorbent pads connected in the form of webs and, if appropriate, equipped with covering webs on both sides, so that a heating to the compacting temperature takes place. The cellular/synthetic pulp mixture is compacted thermally, and at the same time the superabsorbent agent is fixed in at predetermined points of the absorbent pad.

This apparatus is unsuitable for the thermal compacting of individual absorbent pads conveyable at a distance in succession and, if appropriate, also next to one another or covered with a covering web on only one side.

SUMMARY OF THE INVENTION

The object on which the present invention is based is, therefore, to provide an apparatus for the shaping and thermal compacting of absorbent pads for absorbing body fluid and intended for articles of hygiene, which serves for continuous production and in which the absorbent pads can be equipped individually with covering webs either on one side or on both sides, in which the individual production devices are designed so that they can be connected and disconnected for different articles of hygiene in minimum conversion times, and in which the laying-on accuracy even of part layers of differing size will be guaranteed, especially where absorbent pads formed from a plurality of, preferably three, part layers are concerned. At the same time, a feed of superabsorbent agents which is selectable as required will be possible, and the thermal compacting device will be integratable into the apparatus without impairing the production capacity.

The material used for the absorbent pads and referred to as "flocks" preferably consists of a cellular/synthetic pulp mixture, but any other combination would also be possible.

According to the invention, this object is achieved in that at least one rotary band or a plurality of individual rotary bands with receptacles for one or a plurality of absorbent-pad layers has over the entire length of the rotary-band, at distances from one another, trough-shaped insertion molds, into which fit shaping insets, and along the rotary band or the individual rotary bands production devices are arranged in succession in the conveying direction, and in that, furthermore, the thermal compacting device with following calender and/or embossing rollers, which consist of a heating cylinder with a pressure band engaging on it, is arranged in the conveying direction. Advantageous further embodiments of the present invention will appear below.

The advantage of the apparatus according to the invention is that the rotary band having teeth on both surfaces and guided in two planes lying parallel to and above one another on the one hand engages into the teeth of a toothed driving roller via teeth directed to the inner surface and is guided via a further perforated roller, and by means of its teeth located on the outer surface both toothed flock-metering rollers and a driving band are driven non-positively, thereby guaranteeing a perfect shape of the absorbent pads. A work cycle synchronized in this way always guarantees an accurate construction of multi-layer absorbent pads from a plurality of part layers even of different sizes.

A further advantage of an arrangement of this type is that the individual devices, such as flock-metering devices, metering units for a flock-material/superabsorber-powder mixture, a superabsorber-powder spreading device or superabsorber web portions, and the feeding of covering webs on one side or on both sides can be connected or disconnected, as required, without the apparatus having to be converted.

Because the uncompacted absorbent pads are first sucked into the trough-shaped insertion molds via the vacuum chambers arranged in the first plane and subsequently, after rotation of the rotary band through 180°, are sucked out of the insertion molds onto the driving band via the vacuum chamber arranged in the second plane, the absorption properties of the absorbent pad can be influenced on both sides, as required, depending on the adjustable suction effect.

Whenever the article of hygiene to be produced is changed, it is predominantly necessary only to exchange the air-permeable shaping insets insertable into the trough-shaped insertion molds, only short apparatus standstill times being necessary for this. If this is not sufficient, a conversion of the apparatus can be carried out by exchanging the rotary band equipped with insertion molds, in which case only the individual horizontally arranged devices have to be adapted to the insertion molds of the new rotary band.

Especially effective for the most efficient possible conversion to different articles of hygiene is a possible embodiment which is in addition to that of FIG. 1 and in which, instead of one rotary band, a plurality of, for example, three mutually independent individual rotary bands are arranged in succession in the conveying direction, and simple conversion can be carried out by the insertion of insets and/or the exchange of the individual rotary bands.

In an advantageous way, the individual absorbent pads can be equipped individually, on one side or on both sides, with covering webs, preferably non-woven webs, between the rotary band and driving band or between the pressure band and heating cylinder of the thermal compacting device and can be moved further thus.

BRIEF DESCRIPTION OF THE DRAWINGS

The invention is explained in detail below by means of exemplary embodiments with reference to the drawings.

In these:

FIG. 1a shows a partial plan view of the apparatus according to FIG. 1,

FIG. 1b shows a cross-section through a rotary band designed as a toothed belt along the sectional line I—I in FIG. 1, FIG. 1c shows a cross-section of the rotary band along the sectional line II—II in FIG. 1, FIG. 3a shows a partial plan view of the apparatus according to FIG. 3.

DETAILED DESCRIPTION

Figure 1:
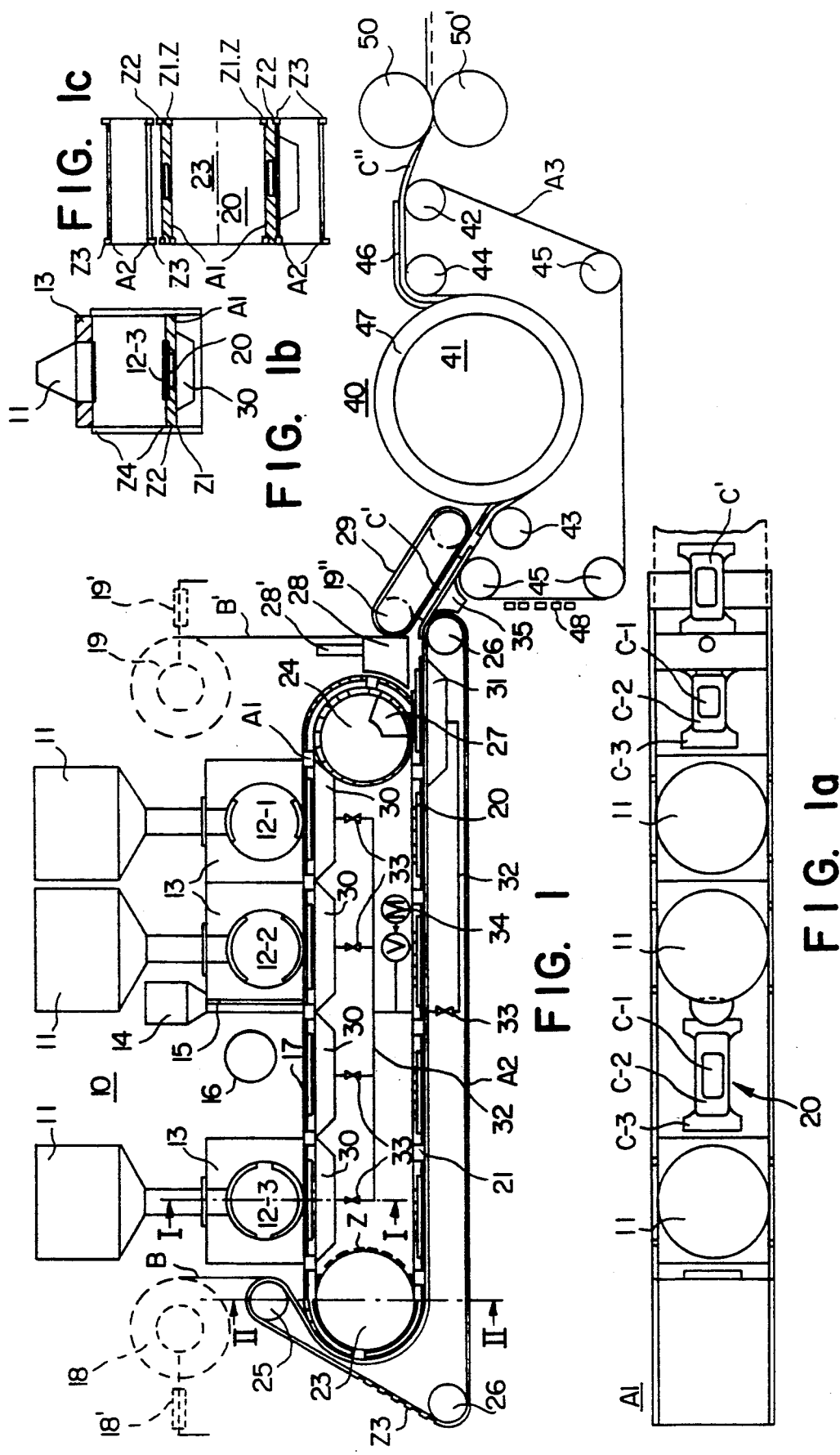
FIG. 1 shows a longitudinal section through the apparatus.

The apparatus according to the invention consists of two processing parts 10 and 40 coupled to one another, specifically of a shaping section 10 and of a thermal compacting section 40. The apparatus 10, 40 can be used in continuously working production lines known per se for the production of articles of hygiene, and the conventional laying-on devices for forming absorbent pads with an appropriate severing device for producing the desired shape, for example for forming the leg portions for napkins, and a conventional thermal compacting device for articles of hygiene guided in the form of webs over perforated drums can be omitted and replaced by the apparatus according to the invention.

According to FIGS. 1, 1a, 1b and 1c, the apparatus 10,40 consists of a rotary band A1 which is equipped in the conveying direction (from right to left in the drawing) with trough-shaped insertion molds 20 at distances from one another. For articles of hygiene of smaller dimensions, the insertion molds 20 in the rotary band A1 could also additionally be arranged at distances next to one another (not shown). Teeth z1, z2 are provided at each of the two edges of the rotary band A1, the rotary band A1 preferably being designed as a toothed belt. In a closed transport loop of the rotary band A1, the production device parts are arranged in two working planes above one another along the path of rotation of the transport band A1.

The rotating rotary band A1 equipped with insertion molds 20 is guided in the upper working plane, in the direction of rotation, past successive production devices 11, 12-1,13,30;11,12-2,13,30; 11,12-3,13,30 for the suction filling of the insertion molds 20 with flock material, for the formation of absorbent pads C, for the feeding of superabsorbent agents in the form of a flock-material/superabsorber-powder mixture via the metering roller 12-2 by means of a metering unit with a spreading device 14,15 or for the feeding of superabsorber web portions by means of a metering unit with an unwinding device 16 and a laying-on device 17. An unwinding device 18 equipped, for example, with a pneumatic brake 18' and intended for feeding a first covering web B, preferably a non-woven web, can be arranged (as represented by broken lines) in the upper working plane after the last production section.

In the return of the rotary band A1, an ejector 27,28,28',31 for shaped absorbent pads C' is arranged in the lower working plane of the shaping apparatus 10. Here, the absorbent pads C' are on the one hand removed from the insertion molds 20 of the rotary band A1 by means of a blow-out device 27 arranged in the perforated roller 24 and on the other hand are removed from the driving band A2 as a result of the suction effect of a vacuum chamber 31. A suction device 28 with a return line 28' ensures freedom from dust. A second covering web B' arranged in front of the thermal compacting part 40 can be fed to the absorbent pads via a deflecting roller 19" by means of a further unwinding device 19,19'. The absorbent pads C,C',C" can be conveyed further individually, equipped with covering webs B,B' on one side or on both sides.

The rotary band A1 is driven by means of a toothed driving roller 23 and is guided via the perforated roller 24. The teeth z of the driving roller 23 engages into the teeth z1 of the rotary band A1. By means of the teet z2 arranged on the outer surface of the rotary band A1, the metering rollers 12-1,12-2,12-3 for the flock material, equipped for this purpose with similar teeth z4, are driven positively, and via a tensioning roller 25 and deflecting rollers 26 the driving band A2 equipped with a similar teeth z3 is positively driven, so that all the important production operations necessary for shaping the absorbent pads C take place in exact synchronism. The individual production devices 11, 12-1,13-30;11,12-2,13,30;14,15;16, 17,30;11,12-3,13,30;18,18';27,28,28'31; 19,19',19"; can be connected and disconnected according to the requirement of the particular article to be processed. Air-impermeable spacer pieces 21 consisting, for example, of an elastic plastic are inserted between the insertion molds 20 in the rotary band A1. The bottoms 20" of the insertion molds 20 are formed by a web, preferably a netted web D, air-permeable over the entire length of the rotary band A1. Depending on the desired shape of the absorbent pad, air-permeable shaping insets 22, preferably consisting of a foam material, are inserted on the bottoms 20" (web D) of the insertion molds 20. The rotary band A1 equipped with insertion molds 20 is described in more detail by reference to FIGS. 2, 2a and 2b.

Arranged in the upper working plane of the rotary band A1, for forming absorbent pads C from at least one layer or, as shown in FIGS. 1 and 1a, from three part layers C-1,C-2,C-3, are production devices 11,12-1,13-30;11,12-2,13,30;11,12-3,13,30; which consist respectively of a supply vessel 11 for the flock material, preferably pulp, produced in suitable mills in material preparation (not shown) and of at least one metering roller 12, in the present case of three metering rollers 12-1,12-2,12-3 which are each arranged in a housing 13 and which interact with a vacuum chamber 30 located underneath the rotary band A1. Each metering roller 12 has teeth z4 (FIGS. 1b, 1c) which is in engagement with the rotary band A1 having the insertion molds 20 by means of the outer teeth z2. The quantity of flock material to be introduced corresponds respectively to the corresponding part volume region 20-1,20-2,20-3 of the insertion molds 20 for the part layer C-1,C-2,C-3 to be filled, that is to say, according to FIGS. 1 and 1a, the filling quantity of the first metering roller 12-1 corresponds to the small part volume region 20-1 of the insertion mold 20 for the small part layer C-1 of the absorbent pad, the quantity from the second metering roller 12-2 corresponds to the larger part volume region 20-2 of the insertion mold 20 for the larger part layer C-2 of the absorbent pad, and that of the third metering roller 12-3 corresponds to the large part volume region 20-3 of the insertion mold 20 for the large part layer C-3 of the absorbent pad. The production sections 12-1,12-2,12-3;13,14;16,17 for forming the absorbent pads C and for applying the superabsorbent agents in the form of a flock-material/superabsorber-powder mixture by spreading or by the laying on of superabsorbent web portions include the vacuum chambers 30 located underneath the rotary band A1 and intended for the retention of the inserted material. In the lower working plane of the shaping apparatus 10, the vacuum chamber 31 located underneath the follower band A2 similarly belongs to the transfer device 27,28,28'. The vacuum chambers 30,31 are connected to a vacuum pump 34 via vacuum lines 32 and valves 33, the vacuum in the individual vacuum chambers 30,31 being controllable, thereby guaranteeing the most efficient possible suction of the absorbent pads or their part layers C-1,C-2,C-3 into the insertion molds 20 or into their part regions 20-1,20-2,20-3 or out of the insertion molds 20.

After the shaped, but still uncompacted absorbent pads C' have been transferred out of the insertion molds 20 from the rotary band A1 onto the follower band A2 by the ejector device 27,28,28',31, they pass into a thermal compacting device 40 which is coupled mechanically to the shaping apparatus 10.

The thermal compacting device 40 consists of a double-walled heating cylinder 41, in which, for example, oil is used as a heating medium. The heating cylinder 41 has partially looping round it in its lower half a pressure band A3 guided via a driving roller 42, a tensioning roller 43 and a deflecting/tensioning roller 44 and via deflecting rollers 45. The absorbent pads C',C" guided between the pressure band A3 and the heating cylinder 41 can run through the thermal compacting device individually, covered with a covering web B or B' on one side or with the two covering webs B,B' on both sides.

In the region of the heating cylinder 41 and of the deflecting/tensioning roller 44 there is a guide 46, so that the absorbent pads C" can be guided in a controlled manner to following calender and/or embossing rollers 50,50'.

An auxiliary transport device 29 is provided between the follower band A2 and the pressure band A3 of the compacting device 40, above the support 35 equipped with a suction device, so that the absorbent pads C' can be conveyed further safely even without covering webs B,B'.

The pressure band A3, preferably designed as a steel band, can be heated on one side or on both sides, preferably on its band face confronting the heating cylinder 41 by means of a heating device 48, for example eddy-current heating, with the result that the thermal compacting (thermobonding) of the cellular/synthetic pulp mixture of the absorbent pads C' can take place in an accelerated manner, with the superabsorbent agent embedded in the absorbent pad being fixed at the same time. The heating device 48 consists of a plurality of units which are arranged over the width of the pressure band and which activatable opposite the associated face of the pressure band in accordance with the shape of the absorbent pad.

If all the articles of hygiene to be produced are also to be compacted thermally, the driving band A2 of the shaping apparatus 10 and the pressure band A3 of the thermal compacting device 40 could be replaced by a common pressure band.

Figure 2:
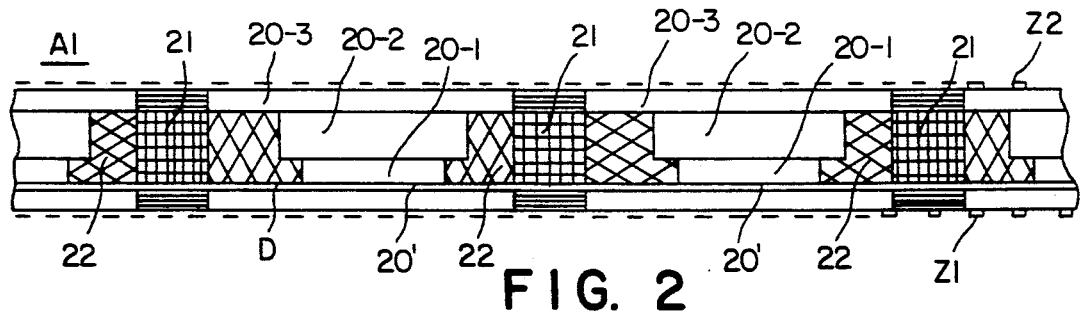
FIG. 2 shows a longitudinal section through the rotary band equipped with insertion molds.
Figure 2A:
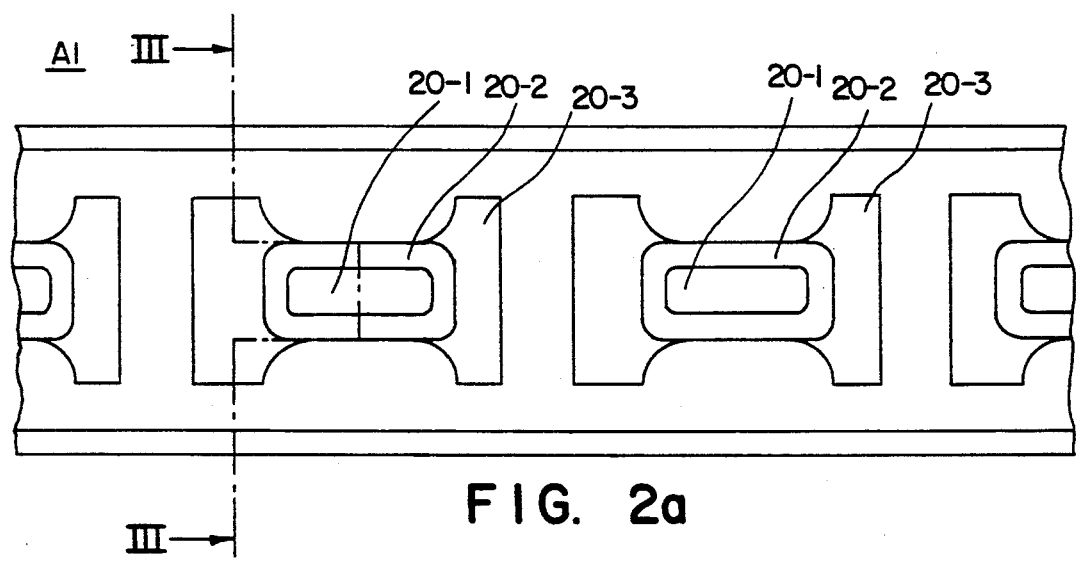
FIG. 2a shows a plan view of the rotary band according to FIG. 2.
Figure 2B:
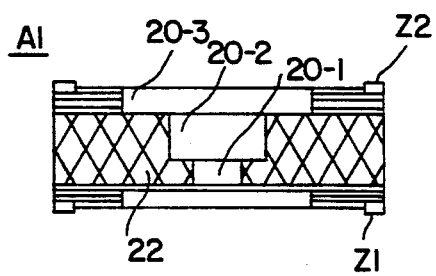
FIG. 2b shows a cross-section of the rotary band along the sectional line III—III in FIG. 2a, FIG. 3 shows a longitudinal section through a development of the apparatus according to FIG. 1

The rotary band A1 designed as a toothed belt is shown in FIGS. 2,2a and 2b on an enlarged scale in relation to FIG. 1. The rotary band A1 has insertion molds 20 which, for example, are suitable for three-layer absorbent pads C consisting of individual part layers C-1,C-2,C-3.

The respective part regions 20-1,20-2,20-3 of the insertion moulds 20, into which the individual layers are inserted, as already described, consist of foam-like shaping insets 22 which are placed on the netted air-permeable web D. The insertion molds 20-1 remaining free of insets 22 form their bottoms 20″. The insets 22 can also be designed so that, depending on the function of the absorbent pad of the article of hygiene, they can be given a plane, inclined, curved, concave or convex and suchlike shape for a body fit, and the particular shape selected can be fixed in the thermal compacting device without any additional measures.

FIGS. 3 and 3a illustrate a design, additional to that of FIGS. 1 and 1b, of a shaping apparatus 10' which is especially suitable for articles of hygiene with a plurality of absorbent-pad part layers C-1,C-2,C-3.

Instead of one rotary band A1 according to FIG. 1, there are used, according to the number of absorbent-pad part layers C-1,C-2,C-3, for example three individual rotary bands A10-1,A10-2,A10-3 which are arranged in succession in the conveying direction above a driving band A20 and in the opposite direction to which and facing which the perforated driving band A20 is provided in synchronism.

The individual rotary bands A10-1,A10-2,A10-3 have at their two edges toothings z5 which engage into the toothings z4' of the deflecting rollers 56'. The production devices (in the conveying direction) 18,8';-11',12'-3,13,30;11',12'-2,13,30;14,15;16,17,30;11',1-2'-1,13,30;19,19',19″ are designed similarly to those shown in FIG. 1 and therefore need not be described in any more detail. Instead of the metering rollers 12-1,12-2,12-3, according to FIG. 1, there are used pairs of metering bands 12'-1,12'-2,12'-3 which interact with the insertion moulds 20'-1,20'-2,20'-3 of the individual rotary bands A10-1,A10-2,A10-3 and with the vacuum chambers 30.

The pairs of metering bands 12'-1,12'-2,12'-3 each consist of two endless bands with scraper pins arranged over the circumference, the flock material passing out of the material preparation (not shown) via a material feed 11' into the housing 13 of the metering unit and being guided in the direction of the arrow between the two endless bands to the insertion moulds 20';20'-1,20'-2,20'-3 of the individual rotary bands A10-1,A10-2,A10-3. The particular endless band located nearer the individual rotary band A10-1,A10-2,A10-3 has a higher rotational speed in relation to the other, so that the interengaging scraper pins of the two endless bands, by scraping off the excess material, guarantee a uniform material layer thickness.

The shaping insets 52 correspond to the shaping insets 22 according to FIG. 1, these being inserted into the insertion molds 20'; 20'-1, 20'-2,20'-3 of the individual rotary bands, as shown in FIG. 3 for the individual rotary bands A10-1 and A10-2. If the individual rotary bands are already being used with adapted insertion moulds 20', as shown by way of example in FIG. 3 for the individual rotary band A10-3, there is no need for the shaping insets 52.

The production sections are arranged above the driving band A20, the difference being that the work is carried out not in two working planes, but in one linear plane, and therefore the conveying direction is opposite to that of FIG. 1. The absorbent-pad part layers C-1,C-2,C-3 do not remain in the trough-shape insertion molds 20 (according to FIG. 1), but are built up gradually on the synchronously running driving band A20, so that the blow-out device 27 and the vacuum chamber 31 (according to FIG. 1) underneath the driving band A2 are omitted. The absorbent-pad part layers C-1,C-2,C-3 built up in layers on the driving band A20 are fed directly as uncompacted absorbent pads C' to the compacting device 40 by means of the auxiliary transport device 29.

The perforated driving band A20 is driven by means of a driving roller 57. By means of a gear wheel transmission, a deflecting roller 56' and a transmission roller 54 with a band transmission A4 are driven via a take-up roller 53. The deflecting roller 56' drives the first individual rotary band A10-3 (in the conveying direction). By means of the band transmission A4, a further deflecting roller 56' is driven via a further transmission roller 54' with a band transmission A4' and drives the second individual rotary band A10-2. By means of the band transmission A4', a further deflecting roller 56' is driven via a further transmission roller 54″ and drives the third individual rotary band A10-1 in synchronism. This ensures that both the individual rotary bands A10-1,A10-2,A10-3 and the perforated driving band A20 run synchronously, thereby guaranteeing a perfect formation and layering of the individual absorbent pads C.

The individual rotary band A10-3 which is the first in the conveying direction, in its working position, is arranged directly above the perforated driving band A20, onto which the third absorbent-pad part layer C-3 is laid. The second individual rotary band A10-2 is arranged at a distance from the driving band A20 corresponding to the thickness of the third part layer, so that the second absorbent-pad part layer C-2 comes to rest exactly on the third part layer C-3. The third individual rotary band A10-1 is arranged at a distance from the driving band A20 corresponding to the thickness of the third and second part layers, so that the first absorbent-pad part layer C-1 too can be laid exactly onto the second part layer C-2. The suction effect of the vacuum chambers 30 is respectively set so that the formation of the absorbent pads C, their transport between the synchronously running individual rotary bands A10-3,A10-2,A10-1 and the driving band A20 and the transfer of the absorbent pads C' to the compacting device 40 by means of the auxiliary transport device 29, as already described, are guaranteed perfectly.

The force transmission of the individual rotary bands A10-1,A10-2,A10-3 is obtained respectively via toothings z5 which are arranged at the two edges of each of these and which are in engagement with the toothed deflecting rollers 56'. The actual individual rotary bands A10-1,A10-2,A10-3 are thereby largely relieved of tension, thus avoiding an undesirable distortion of these. The individual rotary bands A10-1,A10-2,A10-3 are lowered out of their initial positions into the appropriate working positions by means of lifting devices 58.

I claim:

1. Apparatus for the shaping and thermal compacting of absorbent pads for absorbing body fluid, intended for articles of hygiene, which comprises:

at least one rotary belt having a conveying direction and including receptacles for at least one absorbent-pad layer;

trough-shaped molds over the length of the rotary belt spaced from one another;

shaping inserts which fit into said molds;

production devices along said at least one rotary belt arranged in succession in the conveying direction; and a thermal compacting device with at least one of a following calender and a following compacting device, said thermal compacting device including a heating cylinder with a pressure band engaging said cylinder and arranged in the conveying direction.

2. Apparatus according to claim 1, wherein the production devices are arranged in twos along the rotary belt, and wherein in the opposite direction to the rotary belt conveying direction there is a perforated follower band which can be pressed against the rotary belt.

3. Apparatus according to claim 2, wherein the rotary belt has first and second teeth at its edges on both sides thereof, said rotary belt being in engagement via said first teeth with the teeth of a roller, and said second teeth of the rotary belt being in engagement (1) on the one hand with teeth of metering rollers, and (2) on the other hand with teeth of the follower band.

4. Apparatus according to claim 3 wherein a plurality of metering rollers for flock material which interact with corresponding molds, and vacuum chambers, are arranged in the conveying direction of the rotary belt.

5. Apparatus according to claim 4 wherein in the at least one rotary belt, the molds are arranged at distances in succession in the conveying direction and air-impermeable spacer pieces are arranged between the molds.

6. Apparatus according to claim 4 wherein in the at least one rotary belt, the molds are arranged next to and at distances from one another.

7. Apparatus according to claim 4 wherein a metering unit with a spreading device for a superabsorber powder is arranged between two flock-material metering devices in the conveying direction.

8. Apparatus according to claim 4 wherein an unwinding device with a laying-on device for a severable superabsorber web is arranged between two flock-material metering devices in the conveying direction.

9. Apparatus according to claim 1, wherein the production devices are arranged along individual rotary belts, and wherein in the opposite direction to the rotary belt conveying direction there is a perforated driving band which can be pressed against the rotary belt.

10. Apparatus according to claim 9 wherein an individual rotary belt is provided for each absorbent pad layer, and all individual rotary belts have teeth at their edges on both sides thereof which are in engagement with deflecting rollers, wherein the individual rotary belt which is the first in the conveying direction is in engagement with a driving roller of the driving band via a take-up roller, and wherein second and third individual rotary belts are respectively connected to transmission rollers from deflecting rollers by means of transmission bands.

11. Apparatus according to claim 10 including a plurality of pairs of metering bands, which interact with corresponding molds of the individual rotary belts, and vacuum chambers, are arranged in the conveying direction of the individual rotary belts.

12. Apparatus according to claim 1 wherein air-permeable shaping inserts are provided for each mold of the rotary belt.

13. Apparatus according to claim 12 wherein said inserts rest on an air-permeable textile web.

14. Apparatus according to claim 1 wherein the at least one rotary belt is designed as a toothed-belt.

15. Apparatus according to claim 1 wherein a blow-out device is arranged in a lower plane of the apparatus within a perforated toother roller and is arranged in operative connection with a vacuum chamber located underneath a follower band and with a suction device facing the toothed roller on the outside thereof.

16. Apparatus according to claim 1 wherein arranged in the conveying direction in an upper plane of the apparatus, after a last metering roller, is an unwinding device which is equipped with a brake and which is intended for a first covering web introducible via a tensioning roller between the rotary belt and a follower band.

17. Apparatus according to claim 1 wherein arranged in the conveying direction in front of a first pair of metering bands is an unwinding device which is equipped with a brake and which is intended for a first covering web introducible via a deflecting roller in the region of a driving roller between a first individual rotary belt and a driving band.

18. Apparatus according to claim 1 wherein a second unwinding device which is equipped with a brake and which is intended for a second covering web introducible via a deflecting roller between the shaped uncompacted absorbent pads and the heating cylinder is arranged above a deflecting roller of a follower band or of a driving band.

19. Apparatus according to claim 1 wherein at least one covering web on both sides are provided between the pressure band and the heating cylinder of the compacting device.

20. Apparatus according to claim 1 wherein for conveying the individual absorbent pads an auxiliary transport device is arranged between a follower band or a driving band and the pressure band and above these.

21. Apparatus according to claim 1 wherein the pressure band has, at least on its face confronting the heating cylinder, a heating device activatable for a predetermined pressure-band area.

22. Apparatus according to claim 1 wherein a follower band or driving band and the pressure band of the compacting device are produced in one piece.

* * * * *